(12) United States Patent
Heuft et al.

(10) Patent No.: US 7,106,827 B2
(45) Date of Patent: Sep. 12, 2006

(54) DEVICE FOR EXAMINING FILLED CONTAINERS BY MEANS OF X-RAYS AND USE OF THIS DEVICE

(75) Inventors: Bernhard Heuft, Burgbrohl (DE); Wolfgang Polster, Andernach (DE)

(73) Assignee: Heuft Systemtechnik GmbH, Burgbrohl (DE)

(*) Notice: Subject to any disclaimer, the term of this patent is extended or adjusted under 35 U.S.C. 154(b) by 0 days.

(21) Appl. No.: 10/534,653

(22) PCT Filed: Nov. 12, 2003

(86) PCT No.: PCT/EP03/12632

§ 371 (c)(1),
(2), (4) Date: May 12, 2005

(87) PCT Pub. No.: WO2004/044567

PCT Pub. Date: May 27, 2004

(65) Prior Publication Data

US 2006/0056583 A1    Mar. 16, 2006

(30) Foreign Application Priority Data

Nov. 12, 2002  (DE)  .................... 202 17 559 U

(51) Int. Cl.
*G01N 23/04* (2006.01)
(52) U.S. Cl. ........................................................ 378/57
(58) Field of Classification Search ................. 378/57, 378/58; 250/358.1, 359.1, 559.4, 559.41
See application file for complete search history.

(56) References Cited

U.S. PATENT DOCUMENTS

| | | | | |
|---|---|---|---|---|
| 4,025,202 A | 5/1977 | Deane | ..................... | 356/239.4 |
| 6,005,912 A | 12/1999 | Ocleppo | ..................... | 378/57 |
| 2005/0105680 A1* | 5/2005 | Nabors et al. | ................ | 378/57 |

FOREIGN PATENT DOCUMENTS

| | | |
|---|---|---|
| EP | 0 124 164 A1 | 11/1984 |
| EP | 0 604302 A1 | 6/1994 |
| EP | 0 795 746 A1 | 9/1997 |
| EP | 0 961 114 A1 | 12/1999 |
| WO | WO 93/06469 A1 | 4/1993 |
| WO | WO 9306469 A1 * | 4/1993 |
| WO | WO 01/44791 A2 | 6/2001 |
| WO | WO 01/96842 A2 | 12/2001 |

* cited by examiner

*Primary Examiner*—Edward J. Glick
*Assistant Examiner*—Courtney Thomas
(74) *Attorney, Agent, or Firm*—Gardner Carton & Douglas LLP

(57) ABSTRACT

The invention related to a device for examining filled containers for foreign bodies. In an embodiment, the device for examining filled containers for foreign bodies has a transport apparatus for transporting the containers individually in succession in a row on a plane of transport, at least one X-ray source which emits X-rays in a predetermined direction, and an apparatus for recording the X-rays after they have passed through the containers. In an embodiment, the direction in which the X-rays are emitted from the X-ray source is inclined by between 10° and 60° to the plane of transport. In an embodiment, two X-ray sources are provided, namely one arranged above and one below the plane of transport. In an embodiment, the X-ray source is positioned such that the ray course is approximately tangential to the maximum slope of the bulge of the container bottom.

8 Claims, 4 Drawing Sheets

DEVICE FOR EXAMINING FILLED CONTAINERS BY MEANS OF X-RAYS AND USE OF THIS DEVICE

CROSS-REFERENCE TO RELATED PATENT APPLICATIONS

This patent application claims priority from patent application PCT/EP2003/012632 filed Nov. 12, 2003, which claims priority from German Patent Application Number 202 17 559.6, which was filed on Nov. 12, 2002, the entire content of which is herein incorporated by reference.

FIELD OF THE INVENTION

This invention relates to packaging. More particularly, it relates to examining containers for foreign bodies.

BACKGROUND OF THE INVENTION

The examination of goods which are packed in containers, for example, fruit juices in drink bottles, by means of X-rays is a process known in the food industry. Problems arise when checking for foreign bodies that have a higher density than the packed goods and, therefore, fall to the bottom of the containers. In the case of containers with a dished bottom, as is the case with many drink bottles, the foreign bodies slide on the bulge of the container bottom to the inner container edge. There, they are hard to recognize by means of X-rays, as the X-rays must penetrate not only the vertical container wall but also the bottom of the container. During this process the bottles are oriented, because of the bulge of the container bottom, at an angle of, for example, 10° to the dished surface of the container bottom and therefore travel a very long distance inside the container material. An additional attenuation of the X-rays by any foreign bodies present therefore has only relatively little effect and is frequently no longer detectable. Also, unevennesses in the surface of the container bottom can easily be mistaken for a foreign body.

EP-A-0 795 746 discloses examining the containers using two X-rays, one of which points 45° in the direction of transport and the other of which points 45° against the direction of transport, with the result that they are at right angles to each other.

EP-A-0 961 114 discloses turning the containers upside down for this examination so that any foreign bodies present drop down to the top of the container near the closure where they can be recognized with certainty by means of X-rays.

WO 01/44791 discloses tilting the containers sideways by roughly 80° and then examining them for foreign bodies using a vertically directed X-ray.

BRIEF SUMMARY OF THE INVENTION

The invention is directed to a device for examining containers for foreign bodies. In an embodiment, the device comprises a transport apparatus for transporting the containers individually, in succession, in a row on a plane of transport. An X-ray source for emitting an X-ray in a predetermined direction and an apparatus for recording the X-rays after they have passed through the containers are also included.

DETAILED DESCRIPTION OF THE INVENTION

Figure 1:
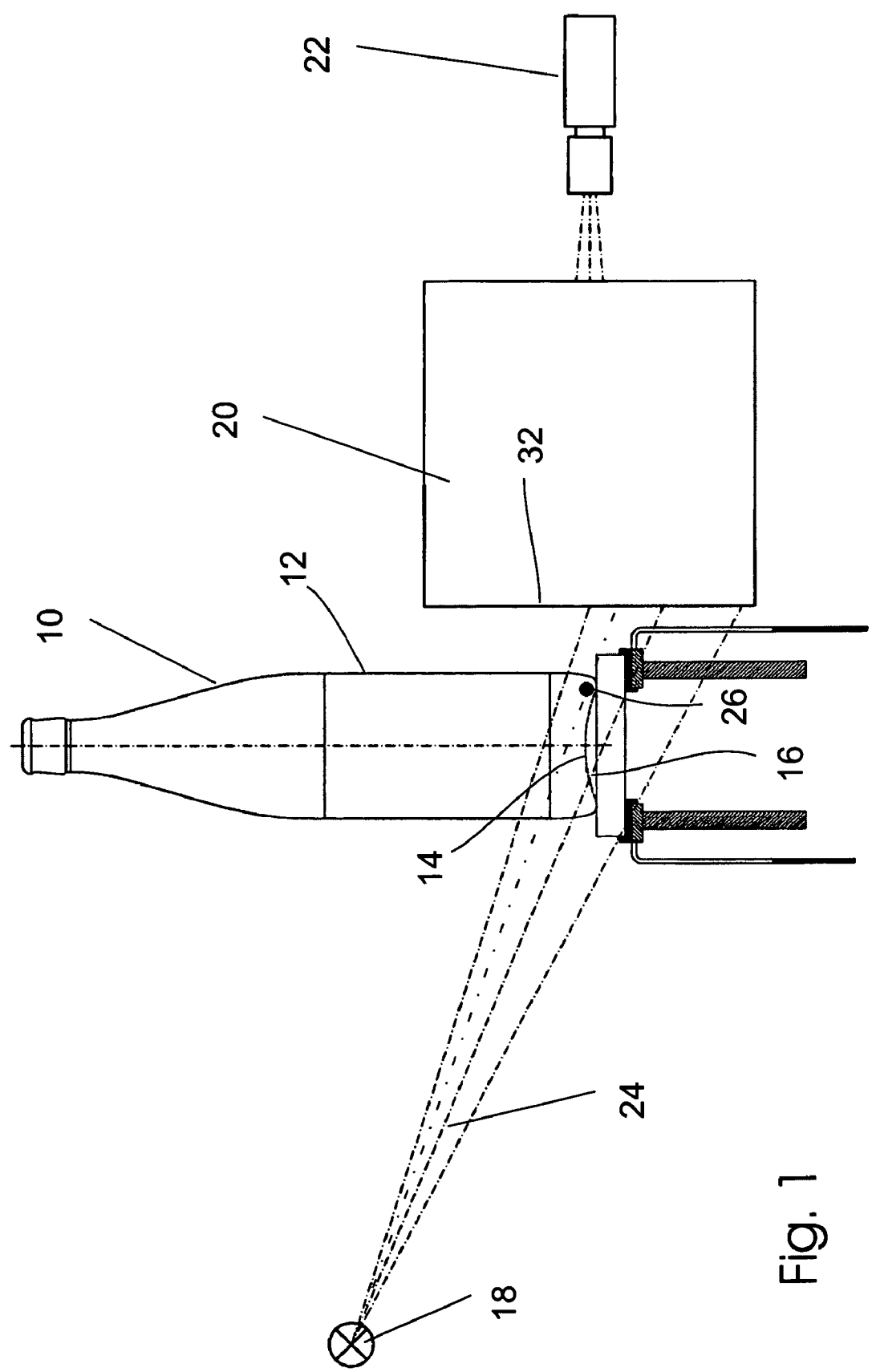
FIG. 1 is a front view of an embodiment of a device according to the invention wherein the X-ray is directed downward at the container at an angle of 30° towards the plane of transport.

As shown in FIGS. 1–4, the invention is directed to an apparatus for the detection of foreign bodies in filled containers. The apparatus will now be described in detail with reference to the figures.

In an embodiment, as shown in FIGS. 1–4, the containers are drink bottles 10 which, in the lower area, have a cylindrical wall 12 and a dished bottle bottom 14. In an embodiment, the bottles 10 are constructed of glass. The bottles 10 are transported standing upright on a transport apparatus 16. The top of the transport apparatus 16 defines a plane of transport. The transport apparatus 16 can be a customary link-chain conveyor with plastic chain links. If the chain links interfere on the X-ray image, a belt conveyor can be used in which the containers 10 are transported by means of two laterally engaging belts. In belt conveyor transport apparatuses, as disclosed in EP-A-0 124 164, the bottom 14 of the containers 10 is not supported. In a belt conveyor transport apparatus, the plane of transport is defined by the container bottoms 10. It preferably lies horizontal. However, it can also be inclined, particularly when using a belt conveyor.

Figure 2:
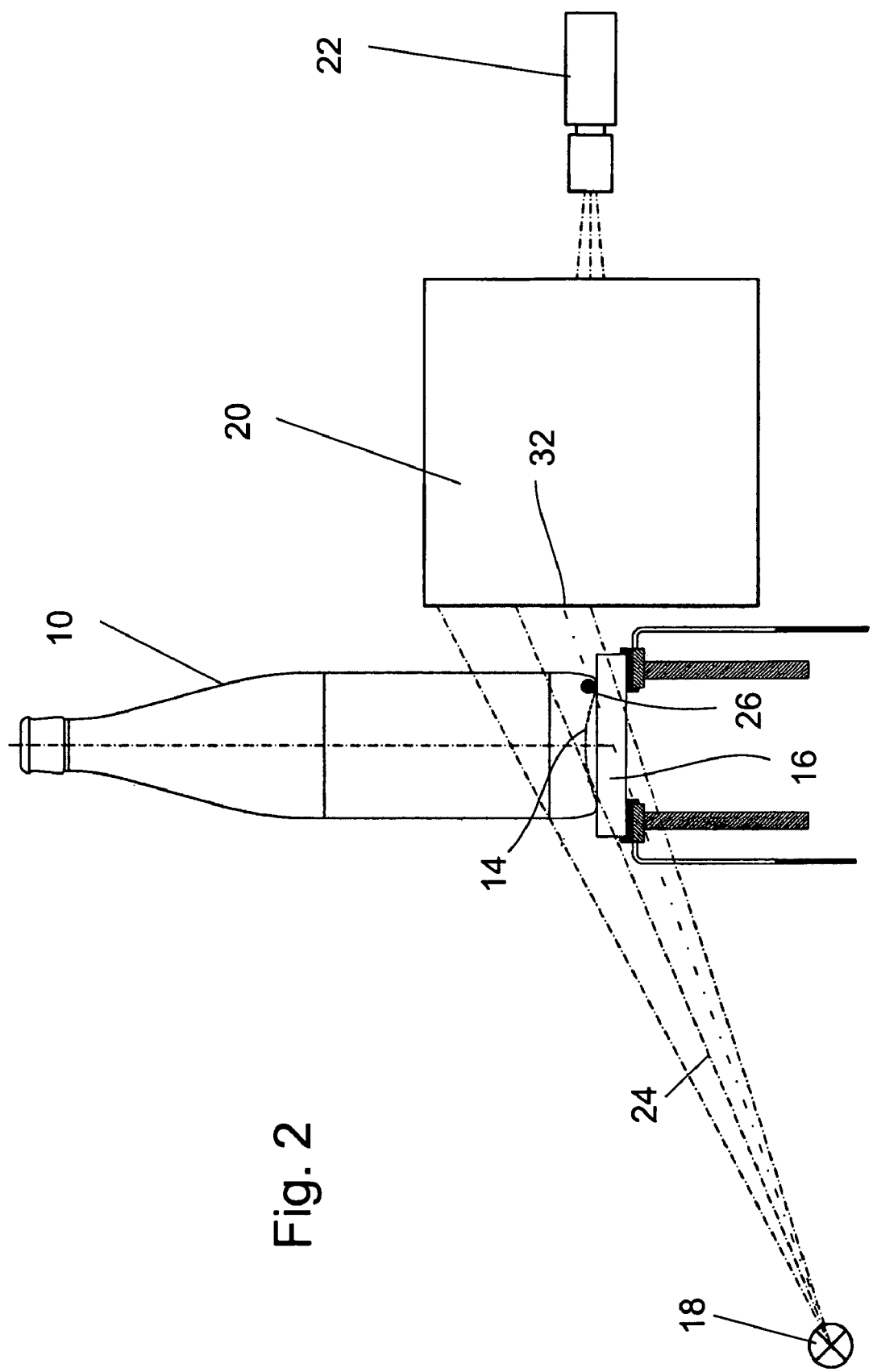
FIG. 2 is a front view of an embodiment of a device according to the invention wherein the X-ray is directed upward at the container at an angle of 30° towards the plane of transport.
Figure 3:
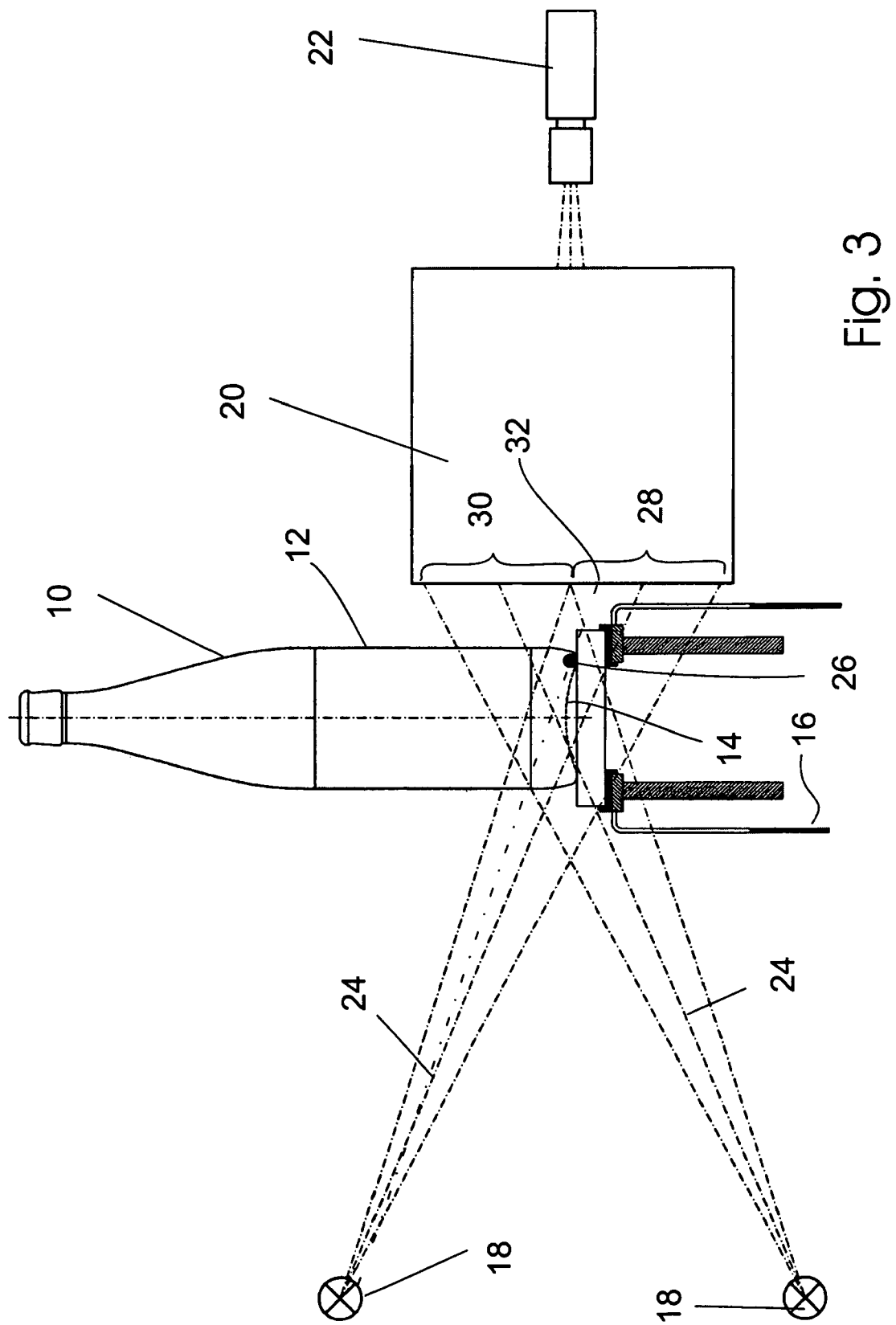
FIG. 3 is a front view of an embodiment of a device according to the invention with two X-rays directed at the container.

An X-ray source 18 is arranged at a distance next to one side of the transport apparatus 16. The X-ray source 18 may produce x-rays 24 of any suitable energy level. Suitable X-ray sources 18 may produce, for example, an X-ray 24 with 50 to 100 keV. In an embodiment, a 60 keV X-ray source 18 is used. Dished container bottoms 14 generally have a maximum slope of between approximately 10° and 60° at the edge. Therefore, in an embodiment, the X-ray source 18 is positioned such that, at the point of the maximum slope of the container bottom 14—which is generally at the edge of the container bottom 14—the course of the X-ray 24 is roughly tangential to the bulge of the container bottom 14, as shown in FIGS. 1-3. This can be achieved by having an X-ray source 18 arranged either above the plane of transport or below the plane of transport. In either case, the X-rays 24 are preferably aligned roughly at a right angle to the direction of transport.

An apparatus for recording the X-rays 24 is on the other side of the transport apparatus 16. The apparatus for recording the X-rays 24 is arranged on the side of the transport apparatus 16 lying opposite the X-ray source 18. This apparatus can be a line of X-ray detectors or a two-dimensional field of X-ray detectors. In an embodiment, the X-ray detectors are photodiodes with a scintillation crystal. In another embodiment, the recording apparatus is an area sensor, for example, an X-ray image converter 20 or an X-ray image intensifier, with a downstream photographing device such as a CCD camera 22. Through the use of such an area sensor, the necessary exposure time is minimized and the exposure of the product and the environment to the ray is thus reduced.

If the X-ray source 18 is arranged above the plane of transport, the upper part of the X-ray 24 travels, in the area of the inner edge of the container bottom 14 facing away from the X-ray source 18, approximately tangentially to the bulge of the container bottom 14. As a result, the X-ray 24 penetrates the material of the container 10 only on the front and on the back of the wall 12, but does not travel an extended distance inside the container bottom 14. If the inclination is, for example, 30°, the section inside the vertical container wall 12 increases by only approximately 15%. Consequently, the contrast of intensity differences that is caused by foreign bodies is reduced only to an insignificant extent.

Similarly favorable conditions apply in the area of the inner edge of the container bottom 14 facing the X-ray source 18. Here the container bottom 14 rises at an angle of, for example, 30°, and so the X-ray 24 then travels at an angle of 60° to the container bottom, with the result being that here too the distance travelled is extended by only approximately 15% compared with an incidence at a right angle.

In the embodiment shown in FIG. 1, the X-ray 24 is inclined by an angle of 30° down towards the plane of transport. The distance between the X-ray source 18 and the transport apparatus 16 is approximately 30 cm and the X-ray 24 has a divergence of 15°, with the result that the whole bottle bottom 14, which has a diameter of approximately 7 cm, lies within the X-ray 24. The X-ray image converter 20 is arranged at the smallest possible distance next to the transport apparatus 16 and covers at least the area of the X-ray 24 which has penetrated the bottle bottom 14.

In the embodiment shown in FIG. 1, there is a foreign body 26, for example, a glass splinter, on the side facing away from the X-ray source 18 of the inner edge of the bottle bottom 14. The foreign body 26 absorbs or scatters the X-rays 24 and can be recognized on the X-ray image converter 20 as a dark spot 32. As can be seen in FIG. 1, the rays in the immediate vicinity of the rays which strike the foreign body 26 penetrate the front and back of the wall 12 of the bottle 10 at an angle of approximately 60°. This also applies to the rays travelling immediately thereunder, which travel approximately tangentially to the bulge of the edge of the bottle bottom 14. On the other hand, the rays lying somewhat deeper travel a relatively long distance inside the bottle bottom 14 and are thereby very markedly attenuated. Unevennesses in the top or bottom of the bottle bottom 14 has a particularly marked effect on the deeper rays. The rays in the immediate surroundings of the foreign body 26 are very uniformly attenuated, however, with the result being that the foreign body 26 can be recognized through a clear brightness contrast on the X-ray image converter 20.

The X-ray 24 can also be directed from below at an angle of, for example, 30° to the plane of transport towards the container bottom 14. In the area of the edge of the container bottom 14 facing the X-ray source 18, the X-ray 24 then travels approximately tangentially to the bulge of the container bottom 14, whereas in the area of the inner edge of the container bottom 14 facing away from the X-ray source 18, it then travels, in the chosen case, at an angle of approximately 60° to the container bottom 14.

In the embodiment shown in FIG. 2, the X-ray source 18 is arranged below the plane of transport, and the X-ray 24 is directed at an angle of 30° upward towards the plane of transport. The same foreign body 26 as in FIG. 1 also stands out clearly against its surroundings in this case. The resulting angle at which the rays in the area surrounding the ray striking the foreign body 26 are directed towards the bottle bottom 14 is 30° plus the slope of the edge of the bottle bottom 14, which is typically also 30°. Any unevennesses in the material thickness in the bottle 10 thus has only a slight effect. As regards the arrangement of the X-ray image converter 20 and the CCD camera 22, the embodiment of FIG. 2 corresponds to that of FIG. 1.

The conditions as regards the course of the X-rays 24 to the bulge of the bottle bottom 14 and to the container walls 12 are transposed in the embodiments of FIGS. 1 and 2 if the foreign body 26 is located on the side of the bottle bottom 14 facing toward the X-ray sources 18 instead of on the side facing away from the X-ray sources 18 of the bottle bottom 14.

In an embodiment of the invention, the containers are examined using two X-rays 24. In this embodiment, one of the X-rays 24 is directed towards the container bottom from above, and the other X-ray 24 is directed towards the container bottom from below. Both X-ray sources 18 are preferably arranged on the same side of the transport apparatus 16. The angles at which the X-rays 24 are directed towards the container bottom 14 can be the same or different. They are preferably approximately 30°. It is also possible to use still further X-ray sources 18, for example a third X-ray source 18 which directs an X-ray parallel to the plane of transport or at a different angle from the first and second X-ray sources 18 onto the container bottom 14. The angle of the X-rays 24 to the direction of transport can also be different.

Figure 4:
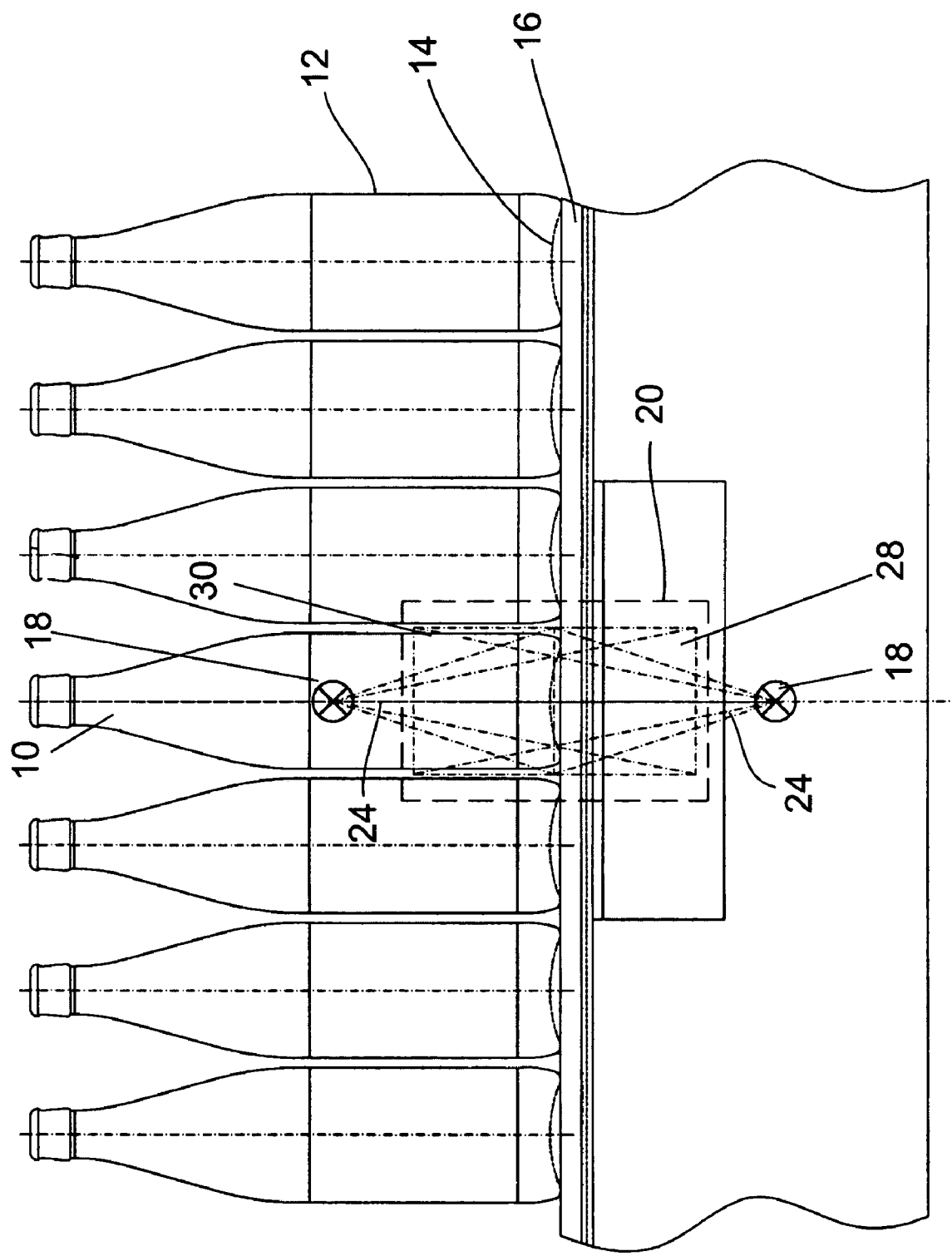
FIG. 4 is a side view of the device of FIG. 3.

FIGS. 3 and 4 illustrate an embodiment in which two X-ray sources 18 are provided. As shown in FIGS. 3–4, the X-ray 24 emitted from the first X-ray source 18 arranged above the plane of transport is directed downward towards the plane of transport at an angle of 30°. The second X-ray source 18 is arranged below the plane of transport, and the X-ray 24 emitted from it is directed upward towards the plane of transport at an angle of 30°.

When using two X-rays 24, the images are preferably coupled on an area sensor. The divergence angle of the X-rays 24 and the distance between the X-ray sources and the transport apparatus 16 on one side and the distance between the area sensor and the transport apparatus 16 on the other side are matched to each other such that the image produced by the X-ray 24 coming from below appears in the upper half of the area sensor, while the image produced by the X-ray 24 coming from above appears in the lower half of the area sensor. Defects which emerge in one image can be sought and confirmed in the other image. As shown in FIGS. 3–4, the distance between the X-ray sources 18 and the transport apparatus 16, the divergence of the emitted X-rays 24, and the size of the X-ray image converter 20 and its distance from the transport apparatus 16 are chosen such that the first image 28 produced by the first X-ray 24 is located in the lower half of the X-ray image converter 20 and the second image 30 produced by the second X-ray 24 is located in the upper half of the X-ray image converter 20. In FIGS. 3–4, the foreign body 26 is again arranged as in FIGS. 1 and 2, and it produces a spot 32 of reduced brightness both in the first image 28 and in the second image 30. In an embodiment, both images are taken using a single CCD camera 22.

An apparatus for recording the X-rays 24 and for evaluating the information is allocated to each X-ray source 18. By comparing the information supplied by the individual recording apparatuses, a three-dimensional position determination of the defects is possible, as a result of which foreign bodies can be distinguished from defects in the material of the container wall 12. The precise spatial position of the foreign body 26 can be established from the position of the two spots 32 using customary image-processing methods. If this position lies on the outside of the wall 12 of the bottle 10, it can be concluded from this that it is not a foreign body 26 inside the bottle 10 but may be, for example, a raised point on the outside of the wall 12. The bottle 10 is then not defective.

As regards the accuracy of recognition and the sharpness of contrast of the spot 32 of reduced intensity caused by the foreign body 26 on the X-ray image converter 20, the same conditions are obtained in the embodiment of FIG. 1 as for the first image 28 of FIG. 3, and the same conditions are obtained as in the embodiment of FIG. 2 in the case of the second image 30. The conditions are again transposed if the foreign body 26 is located on the side of the bottle bottom 14 facing the X-ray sources 18.

The subject-matter of the invention is also the use of the previously described device for examining filled containers 10 for foreign bodies 26, in particular glass bottles 10 with a dished bottom. The X-ray source 18 or the X-ray sources 18 are preferably positioned such that, at the point of the maximum slope of the container bottom 14, the course of the ray is roughly tangential to the bulge of the container bottom 14.

What is claimed is:

1. A device for examining filled containers for foreign bodies, the device comprising:
    a transport apparatus for transporting the containers individually in succession in a row on a plane of transport wherein the plane of transport is substantially horizontal and is defined by a top of the transport apparatus;
    a first X-ray source for emitting an X-ray, wherein the first X-ray source is arranged above the plane of transport and emits X-rays downward towards the plane of transport in a first predetermined direction, wherein the first predetermined direction is inclined by between approximately 10° and approximately 60° to the plane of transport;
    a second X-ray source for emitting an X-ray, wherein the second X-ray source is arranged below the plane of transport and emits X-rays upward towards the plane of transport in a second predetermined direction, wherein the second predetermined direction is inclined by between approximately 10° and approximately 60° to the plane of transport; and
    at least one apparatus for recording the X-rays after they have passed through the containers.

2. The device of claim 1, wherein:
    the at least one apparatus for recording the X-rays after their passage through the containers is a member of a plurality of apparatuses for recording the X-rays;
    one of the plurality of apparatuses is allocated to each X-ray source; and
    the X-rays recorded by the recording apparatuses are compared with one another in an evaluation apparatus.

3. The device of claim 1, wherein the rays of the first and second X-ray sources fall onto, respectively, first and second areas of the apparatus for recording the X-rays.

4. The device of claim 1, wherein the apparatus for recording the X-rays is an X-ray image converter with a downstream digital camera.

5. The device of claim 1, wherein at least one ray source selected from the group consisting of the first X-ray source and the second X-ray course is positioned such that a ray course is approximately tangential to a maximum slope of a bulge of a bottom of the container.

6. A method of examining filled containers for foreign bodies, the method comprising:
    transporting a plurality of filled containers individually in succession in a row on a substantially horizontal plane of transport;
    passing a first container of the plurality of containers through X-rays generated by a first X-ray source positioned above the plane of transport and a second X-ray source positioned below the plane of transport, wherein the X-rays have a first predetermined direction from the first X-ray source and a second predetermined direction from the second X-ray source, wherein the first predetermined direction of the X-rays is inclined by an angle to the plane of transport, the angle measuring approximately between 10° to 60° and the second predetermined direction of the X-rays is inclined by an angle to the plane of transport, the angle measuring approximately between 10° to 60°; and
    recording the X-rays after they pass through the first container.

7. The method of claim 6, wherein:
    a ray source selected from the group consisting of the first X-ray source and the second X-ray source is positioned such that a ray course is approximately tangential to a maximum slope of a bulge of a bottom of the first container.

8. The method of claim 6, wherein the step of recording the X-rays after they pass through the first container is performed by an X-ray image converter and a digital camera.

* * * * *